United States Patent [19]
Shirley

[11] Patent Number: 5,857,988
[45] Date of Patent: Jan. 12, 1999

[54] LATERALLY ADJUSTABLE KNEE BRACE

[75] Inventor: Terry L. Shirley, Laguna Hills, Calif.

[73] Assignee: Tagg Industries, L.L.C., Laguna Hills, Calif.

[21] Appl. No.: 874,206

[22] Filed: Jun. 13, 1997

[51] Int. Cl.[6] .................................................. A61F 5/00
[52] U.S. Cl. .............................................. 602/26; 607/16
[58] Field of Search .................... 607/26, 16, 5, 607/23, 32, 36; 482/124

[56] References Cited

U.S. PATENT DOCUMENTS

| | | | |
|---|---|---|---|
| 2,195,024 | 3/1940 | Bullock | 602/26 |
| 4,433,679 | 2/1984 | Mauldin et al. | 602/26 X |
| 5,013,037 | 5/1991 | Stermer | 602/26 X |
| 5,599,288 | 2/1997 | Shirley et al. | 602/26 |
| 5,662,595 | 9/1997 | Chesher et al. | 602/20 |

*Primary Examiner*—Richard J. Apley
*Assistant Examiner*—Denise Pothier
*Attorney, Agent, or Firm*—Harry G. Weissenberger

[57] ABSTRACT

In a cable-based external knee ligament system, tensioned cables are disposed in a zig-zag pattern on each side of the femoral, patellar and tibial areas, and the load on selected ligaments can be varied by laterally moving cable guides above and below the knee which form the zig-zag pattern.

8 Claims, 3 Drawing Sheets

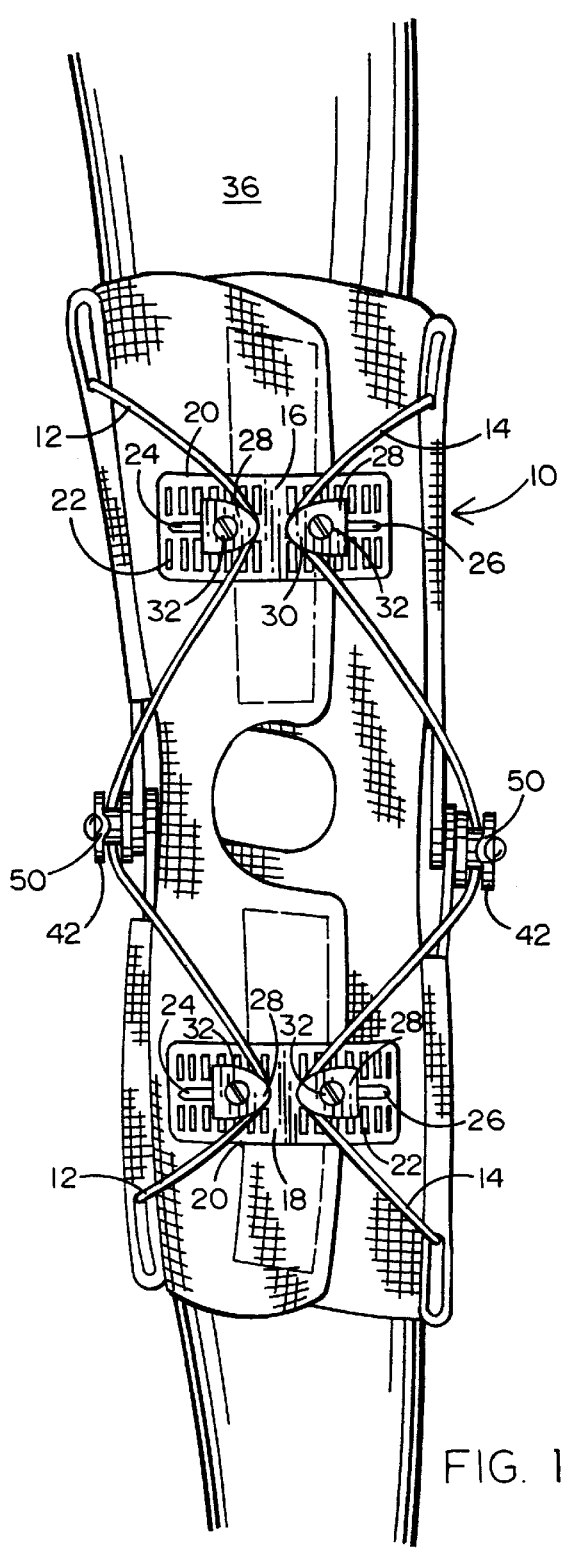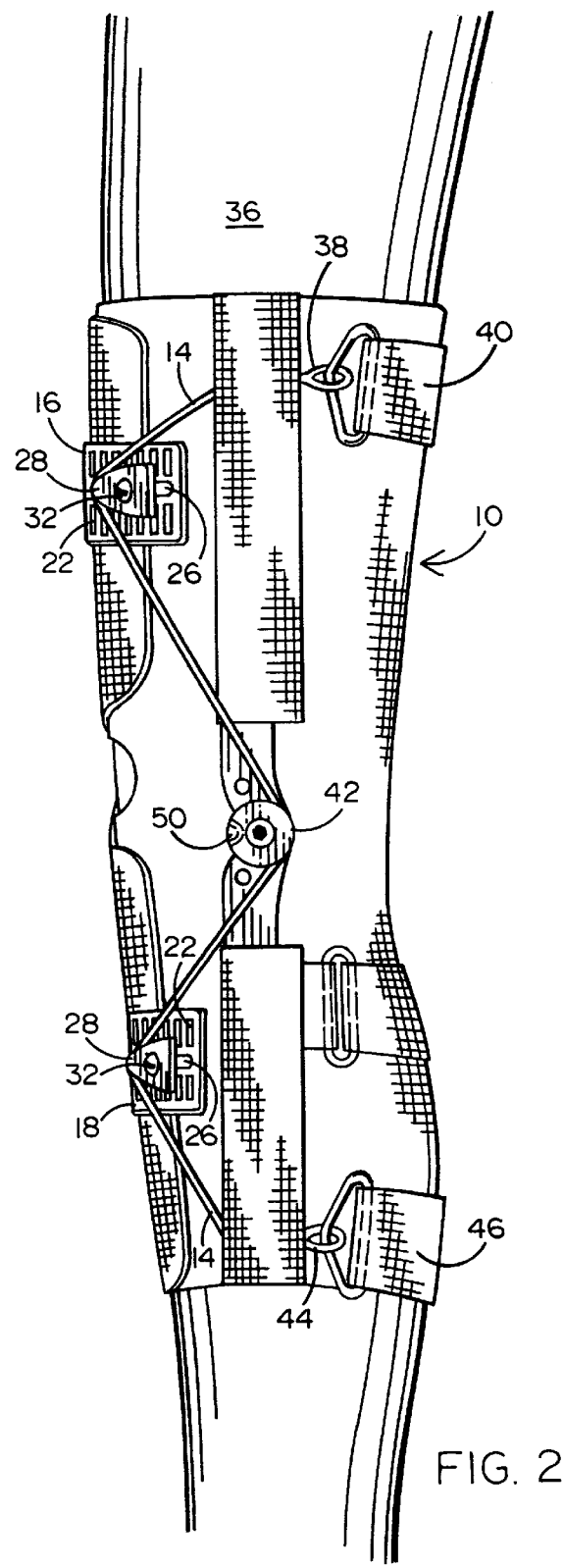

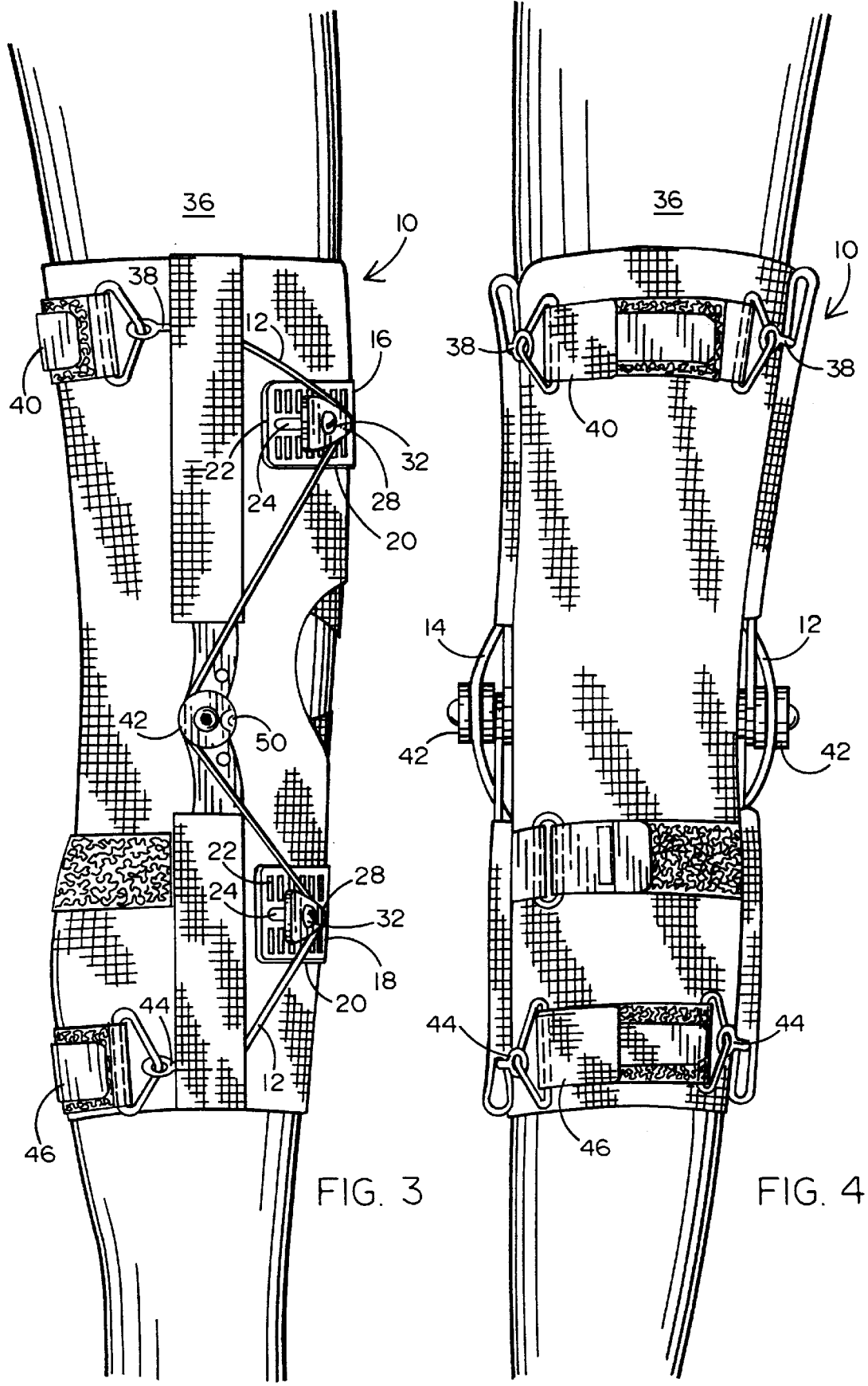

LATERALLY ADJUSTABLE KNEE BRACE

FIELD OF THE INVENTION

This invention relates to orthopedic knee braces, and more particularly to a lightweight cable-tensioned brace in which the cable load is laterally adjustable.

BACKGROUND OF THE INVENTION

U.S. Pat. No. 5,599,288 issued 04 Feb. 1997 to Shirley et al. and entitled "External Ligament System" discloses a lightweight flexible knee brace in which a pair of cables secured at the back of the wearer's leg extend in criss-cross fashion across the front of the thigh and calf just above and below the knee. A significant part of the brace's action in supporting the knee and its ligaments is the pressure exerted on the front of the thigh and calf by pressure pads that are pressed against the thigh and calf by the cables at the laterally centered points where the cables cross.

It has now been found that the laterally central location of the pressure pads is not necessarily the ideal therapeutic location. The pain associated with osteoarthritis can in many cases be reduced or eliminated by providing a lateral force on the bone of the leg. For some individuals, pressure is best applied somewhat to the right of center, for others somewhat to the left. The brace of U.S. Pat. No. 5,599,288 does not, however, lend itself to lateral load adjustments.

SUMMARY OF THE INVENTION

The present invention allows lateral adjustment of the cable load positions above and below the knee without forgoing the advantages of the cable structure of U.S. Pat. No. 5,599,288, by disposing the cables in a zigzag pattern on each side of the knee, and threading them around cable guides that are mounted on centrally located pressure pads but are laterally movable on the pads.

BRIEF DESCRIPTION OF THE DRAWINGS

FIGS. 1–4 are front, left, right and rear elevations of the inventive brace in place on a patient's leg;

DESCRIPTION OF THE PREFERRED EMBODIMENT

FIGS. 1–4 show the brace 10 of this invention as applied to a patient's leg. Except for the positioning of the tensioning cables 12, 14 and the structure of the load-distributing pressure pads 16, 18, the brace 10 is identical to the brace described in U.S. Pat. No. 5,599,288, whose disclosure is incorporated herein by reference.

Figure 5:
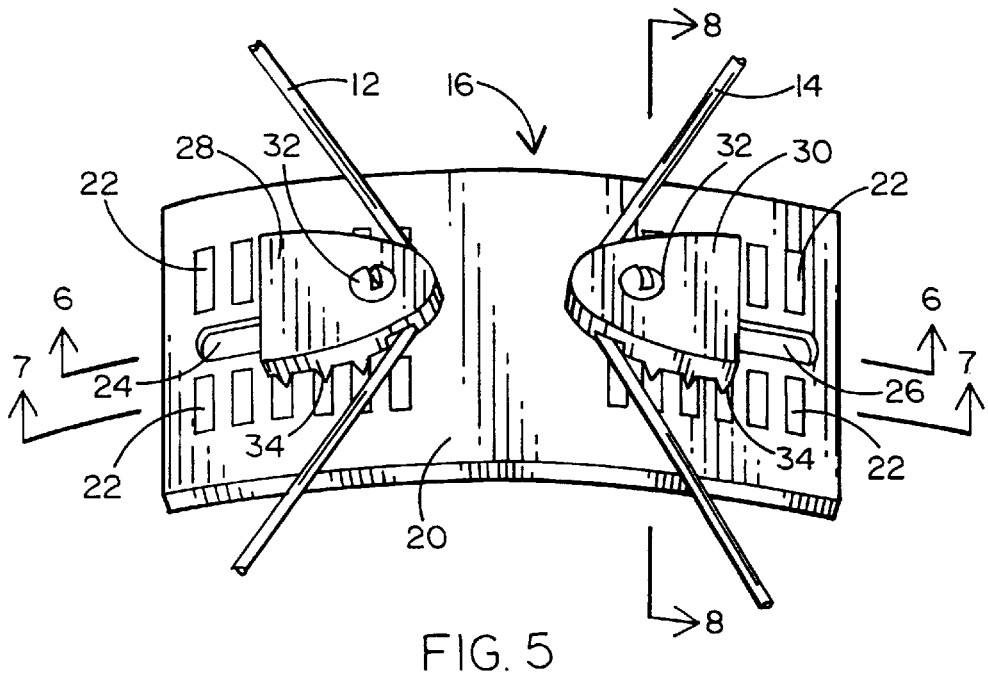
FIG. 5 is a perspective view of the pressure pad of this invention.
Figure 6:
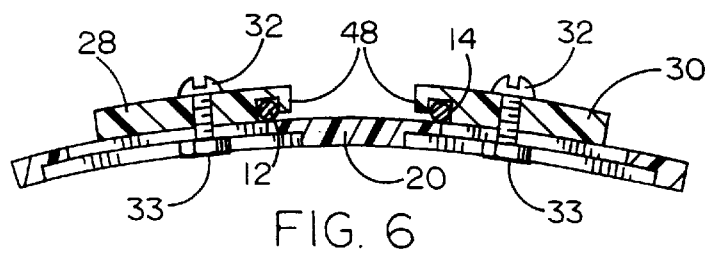
FIG. 6 is a section along line 6—6 of FIG. 5.
Figure 7:
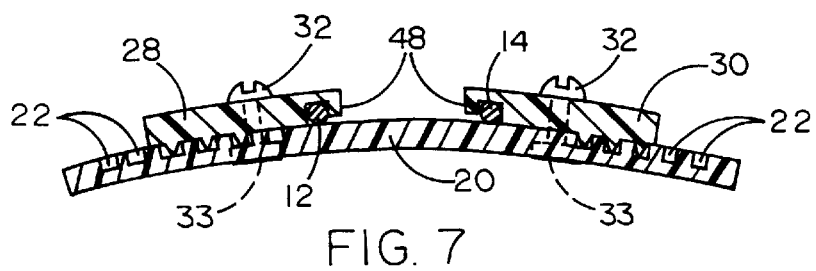
FIG. 7 is a section along line 7—7 of FIG. 5.
Figure 8:
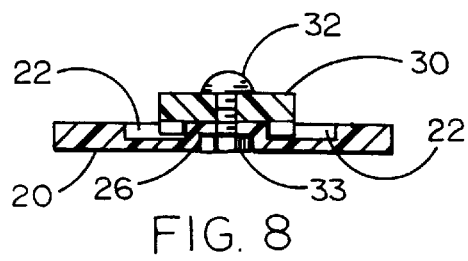
FIG. 8 is a section along line 8—8 of FIG. 5.

In accordance with the present invention, the pressure pads 16, 18 are constructed as best shown in FIGS. 5 through 8. The base 20 of pads 16, 18 is formed of a hard yet somewhat flexible plastic and is curved to generally fit the curve of the wearer's leg surface. The base 20 has four laterally extending sets of grooves 22 formed therein on its outer side for a purpose described below. Laterally extending slots 24, 26 on each side of the base 20 provide tracks in which cable guides 28, 30 are mounted for selective lateral positioning with respect to base 20.

The cable guides 28, 30 are held in the slots 24, 26 by screws 32 and sliding nuts 33 which can be loosened to allow movement of the cable guides 28, 30 in the slots 24, 26, or tightened to prevent movement by engaging the teeth 34 on the cable guides 28, 30 which functions as a direction-changing means for the cable 12 or 14, with the grooves 22. Because the cable guides 28, 30 are subjected to a laterally outwardly directed force by the cables 12, 14, the inclination of the laterally inward-facing faces of the grooves 22 and the laterally outward-facing faces of the teeth 34 is preferably steeper than the inclination of the corresponding outward-facing faces of the grooves 22 and inward-facing faces of the teeth 34, to prevent slippage.

On each side of the leg 36, the cables 12, 14 extend from an anchor point 38 on the upper tensioning strap 40 around the inward end of the upper cable guides 28, 30, then around the flexure axis roller 42 and the lower cable guides 28, 30 to the anchor point 44 on the lower tensioning strap 46.

Protuberances 48 on the cable guides 28, 30 and deformations 50 on the rollers 42 prevent the cables 12, 14 from slipping out of the cable guides 28, 30 and rollers 42 when they are slack.

Based on his evaluation of the patient, the orthopedic surgeon will determine optimum points of force application on the calf and thigh and adjust the position of the cable guides 28, 30 on the pressure pads 16, 18. By doing so, the surgeon can regulate the load applied to the various ligaments of the knee to provide maximum comfort to the wearer of the brace 10.

In use, the brace 10 is circumferentially folded over the wearer's leg 36 as shown in U.S. Pat. No. 5,559,288, and the cables 12, 14 are tensioned or tightened by pulling the anchor points 38 and 44, respectively, toward each other with the aid of Velcro-surfaced straps 40 and 46. The brace 10 is then also secured tightly to the calf just below the knee by tightening support strap 52.

It is understood that the exemplary laterally adjustable knee brace described herein and shown in the drawings represents only a presently preferred embodiment of the invention. Indeed, various modifications and additions may be made to such embodiment without departing from the spirit and scope of the invention. Thus, other modifications and additions may be obvious to those skilled in the art and may be implemented to adapt the present invention for use in a variety of different applications.

I claim:

1. A laterally adjustable knee brace, comprising:
   a) an elongated sheet of flexible material having sides and a top and bottom and having, in its longitudinal direction, a femoral portion, a knee portion, and a tibial portion;
   b) fastening means arranged to secure said sides of said sheet together when said sheet is wrapped around a user's leg to form a sheath, with said sheet's femoral, knee and tibial portions surrounding, respectively, the femoral area, the knee, and the tibial area of the leg;
   c) first and second pressure pads disposed on the front, respectively, of said femoral and tibial portions; each of said pressure pads having first and second cable guides movably mounted thereon;
   d) a first cable arranged to extend, respectively, from a first side of the leg in said femoral portion around said first cable guide of said first pressure pad, to the first side of the leg in the knee portion, thence to said first cable guide of said second pressure pad and back to the first side in said tibial portion;
   e) a second cable arranged to extend, respectively, from a second side of the leg in said femoral portion around said second cable guide of said first pressure pad, to the second side of the leg in the knee portion, thence to said second cable guide of said second pressure pad and back to the second side in said tibial portion; and f) at least one tensioning strap engaging at least one of said cables on said brace arranged to selectively tension said cables.

2. The brace of claim 1, further comprising:

g) substantially rigid linkage means attached to said sheet and extending substantially longitudinally thereof in a position where, when said sheet is wrapped around the leg, said linkage means will be on opposite sides of the knee, said linkage means being hinged in said knee portion.

3. The brace of claim 2, in which said linkage means are movably attached to said sheet, and in which said brace further comprises:

h) an adjustable strap interconnecting said linkage means in the rear of the leg below the knee but above the calf of the leg.

4. The knee brace of claim 2, in which said linkage means include cable guides substantially adjacent the extremities of the linkage means, said cable guides being configured so that said cable means can slide substantially freely therethrough but have limited vertical mobility at said linkage means.

5. The knee brace of claim 1, in which the sides of said sheet are recessed in the knee portion so as to leave the patella uncovered when said sheet is wrapped around the leg.

6. The brace of claim 1, in which said first and second cable guides are mounted on said pressure pads in laterally spaced relation to each other, and are selectively movable in a lateral direction with respect to said pressure pads and to each other.

7. The brace of claim 6, in which said cable guides are slidable in laterally extending slots in said pressure pads and are lockable against movement by an interengageable tooth-and-slot arrangement on said cable guides and pressure pads.

8. An external ligament system for bracing a leg comprising:

a) a brace having a femoral area, a patellar area and a tibial area;

b) a first cable extending from a first point on a first side of said femoral area, to a first direction-changing means on the front of the leg in said femoral area and on to said first side of the patellar area, thence to a second direction-changing means on the front of the leg in said tibial area and on to a second point on said first side of said tibial area;

c) a second cable extending from a third point on a second side of said femoral area, to a third direction-changing means on the front of the leg in said femoral area and on to said second side of the patellar area, thence to a fourth direction-changing means on the front of the leg in said tibial area and on to a fourth point on said second side of said tibial area;

d) retaining means on each side of said patellar area for impeding lateral movement of said cables at the sides of said patellar area;

e) tensioning means for tensioning said cables; and f) means for securing said tensioning means to the leg and for securing said cables to the leg at said points; and g) said first, second, third and fourth direction changing means being cable guides mounted for selective lateral movement.

\* \* \* \* \*